United States Patent
Nadau-Fourcade et al.

(10) Patent No.: US 11,446,272 B2
(45) Date of Patent: *Sep. 20, 2022

(54) BPO WASH EMULSION COMPOSITION

(71) Applicant: Galderma Holding SA, La Tour-de-Peilz (CH)

(72) Inventors: Karine Nadau-Fourcade, Villeneuve-Loubet (FR); Laetitia Mazeau, Cagnes-sur-Mer (FR)

(73) Assignee: Galderma Holding SA, Zug (CH)

(*) Notice: Subject to any disclaimer, the term of this patent is extended or adjusted under 35 U.S.C. 154(b) by 212 days.

This patent is subject to a terminal disclaimer.

(21) Appl. No.: 14/442,698

(22) PCT Filed: Nov. 13, 2013

(86) PCT No.: PCT/EP2013/073738
§ 371 (c)(1),
(2) Date: May 13, 2015

(87) PCT Pub. No.: WO2014/076136
PCT Pub. Date: May 22, 2014

(65) Prior Publication Data
US 2016/0206590 A1  Jul. 21, 2016

Related U.S. Application Data

(60) Provisional application No. 61/725,957, filed on Nov. 13, 2012.

(51) Int. Cl.
| | | |
|---|---|---|
| *A61K 31/327* | (2006.01) | |
| *A61Q 19/10* | (2006.01) | |
| *A61K 8/27* | (2006.01) | |
| *A61K 8/365* | (2006.01) | |
| *A61K 8/38* | (2006.01) | |
| *A61K 8/46* | (2006.01) | |
| *A61Q 19/00* | (2006.01) | |
| *A61K 8/63* | (2006.01) | |
| *A61K 8/60* | (2006.01) | |

(52) U.S. Cl.
CPC ........... *A61K 31/327* (2013.01); *A61K 8/27* (2013.01); *A61K 8/365* (2013.01); *A61K 8/38* (2013.01); *A61K 8/463* (2013.01); *A61K 8/466* (2013.01); *A61K 8/602* (2013.01); *A61K 8/63* (2013.01); *A61Q 19/10* (2013.01); *A61Q 19/008* (2013.01)

(58) Field of Classification Search
CPC ........ A61K 31/327; A61K 8/27; A61K 8/365; A61K 8/38; A61K 8/463; A61K 8/466; A61K 8/602; A61K 8/63; A61Q 19/10; A61Q 19/008; A61P 17/10
See application file for complete search history.

(56) References Cited

U.S. PATENT DOCUMENTS

| | | | |
|---|---|---|---|
| 3,141,821 A | 7/1964 | Compeau | |
| 3,535,422 A | 10/1970 | Cox et al. | |
| 4,056,611 A | 11/1977 | Young | |
| 5,635,469 A * | 6/1997 | Fowler | A61K 8/046 239/329 |
| 6,403,110 B1 * | 6/2002 | Siddiqui | A61K 8/27 424/401 |
| 2002/0111281 A1 | 8/2002 | Vishnupad | |
| 2002/0197228 A1 | 12/2002 | Lasala et al. | |
| 2004/0156873 A1 | 8/2004 | Gupta | |
| 2004/0228885 A1 * | 11/2004 | Khaiat | A61K 8/368 424/401 |
| 2008/0193405 A1 | 8/2008 | Mukherjee et al. | |
| 2009/0035233 A1 | 2/2009 | Spindler et al. | |
| 2009/0318550 A1 * | 12/2009 | Mallard | A61Q 19/08 514/533 |
| 2010/0143285 A1 | 6/2010 | Mallard et al. | |
| 2010/0160439 A1 | 6/2010 | Mallard | |
| 2010/0221245 A1 | 9/2010 | Kunin | |

(Continued)

FOREIGN PATENT DOCUMENTS

| | | | |
|---|---|---|---|
| CN | 101288640 | 10/2008 | |
| EP | 0737474 A2 * | 10/1996 | A61K 8/37 |

(Continued)

OTHER PUBLICATIONS

International Search Report dated Mar. 3, 2014 corresponding to International Patent Application No. PCT/EP2013/073738, 4 pages.

(Continued)

*Primary Examiner* — Kara R McMillian
(74) *Attorney, Agent, or Firm* — Sunit Talapatra; Foley & Lardner LLP

(57) ABSTRACT

A topical dermatological/pharmaceutical composition is described that includes BPO wherein the composition is a wash composition with desirable tolerance, stability and foaming properties. The composition can include: a) benzoyl peroxide (BPO); b) at least one anionic and/or non-ionic surfactant, selected from zinc coceth sulfate; sodium cocoyl isethionate, sodium lauroyl isethionate, C14-C16 α-olefinsulfonates, preferably its sodium salt and decyl glucoside; c) zinc gluconate; d) dipotassium glycyrrhizate; e) an oily phase; f) an aqueous phase; and g) at least one non-ionic emulsifier from the family of sugar ester derivatives, and/or polyglycerol esters and/or gemini surfactants. The composition is preferably in the form of an oil in water emulsion. Also described, is the use of such composition for the treatment of dermatological disorders, and in particular in the treatment of acne.

21 Claims, No Drawings

(56) References Cited

U.S. PATENT DOCUMENTS

| | | | |
|---|---|---|---|
| 2010/0226948 A1 | 9/2010 | Jitpraphai et al. | |
| 2011/0003894 A1* | 1/2011 | Louis | A61Q 19/08 |
| | | | 514/569 |
| 2011/0007183 A1 | 1/2011 | Kahlman | |
| 2011/0045037 A1 | 2/2011 | Tamarkin et al. | |
| 2016/0287703 A1* | 10/2016 | Nadau-Fourcade | A61K 8/27 |

FOREIGN PATENT DOCUMENTS

| | | |
|---|---|---|
| EP | 0 981 325 | 3/2000 |
| EP | 2 005 942 | 12/2008 |
| FR | 2804321 A1 | 3/2011 |
| JP | H10-316555 A | 12/1998 |
| JP | 2009-517429 A | 4/2009 |
| KR | 20110030812 A | 3/2011 |
| WO | WO-98/51275 | 11/1998 |
| WO | WO-2007/062995 A2 | 6/2007 |
| WO | WO-2010/063674 | 6/2010 |
| WO | WO-2011/007183 A2 | 1/2011 |
| WO | 2012/001082 A2 | 1/2012 |
| WO | WO 2012/163928 A2 * | 12/2012 |

OTHER PUBLICATIONS

Written Opinion of the International Searching Authority dated Mar. 3, 2014 corresponding to International Patent Application No. PCT/EP2013/073738, 9 pages.

Bigotti, et al. "Zinc and its Derivatives: Their Applications in Cosmetic"; J. Appl. Cosmetol., (2005), vol. 23, pp. 139-147.

Cosmetics & Toiletries Formulations Database, "Acne Cleanser", William Andrew Publishing, 2005, 1 page.

Cosmetics Business, "in-cosmetics 2009—the cream of the crop", retrieved from: "https://www.cosmeticsbusiness.com/news/article_page/incosnnetics_2009_the_cream_of_the_crop/49283", Apr. 18, 2010, 11 pages.

Dermastir, "Dermastir Ampoules—Zinc Gluconate", retrieved from: "https://www.dermastir.com/skincare-shop/dermastir-ampoules-zinc-gluconate", first published on internet Dec. 15, 2006.

Fishman, "The Mild Surfactant Is Ideal for Body Care", Happi, retrieved from: "https://www.happi.com/contents/view_gleams-and-notions/2011-04-05/this-mild-surfactant-is-ideal-for-body-care-80722", Apr. 5, 2011.

J. Hibbs, "Anionic surfactants", Chemistry and Technology of Surfactants, Ch. 4, vol. 91.

Pascoe, "Cetaphil DermaControl Oil Control Foam Wash and Moisturizer for Oily Skin" Rosacea Support Group, Apr. 26, 2012, downloaded on Jul. 20, 2017 from "rosacea-support.org/cetaphil-dermacontrol-oil-control-foam-wash-and-moisturizer-for-oilyskin.html", 4 pages.

Robinson, et al. "Final report of the amended safety assessment of sodium laureth sulfate and related salts of sulfated ethoxylated alcohols", International Journal of Toxicology, vol. 29(4 suppl), pp. 151S-161S.

Tanghetti et al., "A Current Review of Topical Benzoyl Peroxide: New Perspectives on Formulation and Utilization", Dermatologic Clinics, Jan. 2009, vol. 27(1 ), pp. 17-24.

Truth in Aging, "Dipotassium glycyrrhizate", truthinaging.com, captured by Internet Archive Waybackmachine on Oct. 26, 2011, retrieved from "https://web.archive.org/web/20111026213509/https://www.truthinaging.com/ingredients/dipotassium-glycyrrhizate" on Nov. 10, 2018.

U.S. Appl. No. 14/122,955, filed Jan. 16, 2014.
U.S. Appl. No. 14/442,693, filed May 13, 2015.
U.S. Appl. No. 15/955,371, filed Apr. 17, 2018.

* cited by examiner

BPO WASH EMULSION COMPOSITION

CROSS-REFERENCE TO PRIOR APPLICATIONS

This application is a National Stage of PCT/EP2013/073738, filed Nov. 13, 2013, and designating the United States (published on May 22, 2014, as WO 2014/076136 A1), which claims priority under 35 U.S.C. § 119 to United States Provisional Patent Application No. 61/725,957, filed Nov. 13, 2012, each hereby expressly incorporated by reference in its entirety and each assigned to the assignee hereof.

The present invention relates to compositions for topical application, and to the uses thereof as cosmetic or pharmaceutical products, said compositions being used for the treatment of dermatological disorders, and in particular in the treatment of acne.

Acne is a common multi-factor pathology that attacks skin rich in sebaceous glands (face, shoulder area, arms and intertriginal areas). It is the most commonly occurring form of dermatosis. The following five pathogenic factors play a determining role in the formation of acne:
1. Genetic predisposition,
2. Overproduction of sebum (seborrhoea),
3. Androgens,
4. Follicular keratinization disorders (comedogenesis), and
5. Bacterial colonization and inflammatory factors.

There are several forms of acne, the common factor of all being attack of the pilosebaceous follicles. Mention may be made in particular of acne conglobata, cheloid acne of the nape of the neck, acne medicamentosa, recurrent miliary acne, necrotic acne, neonatal acne, premenstrual acne, occupational acne, acne rosacea, senile acne, solar acne and common acne.

Common acne, also known as polymorphic juvenile acne, is the most common. It comprises four stages:
Stage 1 corresponds to comedonic acne characterized by a large number of open and/or closed comedones and of microcysts;
Stage 2, or papulopustular acne, is of mild to moderate seriousness. It is characterized by the presence of open and/or closed comedones, of microcysts, but also of red papules and pustules. It mainly affects the face and leaves few scars;
Stage 3, or papulocomedonic acne, is more serious and extends to the back, the chest and the shoulders. It is accompanied by a large number of scars;
Stage 4, or nodulocystic acne, is accompanied by numerous scars. It exhibits nodules and also painful voluminous crimson pustules.

The various forms of acne described above can be treated with active agents such as anti-seborrheic agents and anti-infectives, for example benzoyl peroxide (in particular the product Eclaran® sold by the company Pierre Fabre), with retinoids such as tretinoin (in particular the product Retacnyl® sold by Galderma) or isotretinoin (the product Roaccutane® sold by Roche Laboratoires), or else with naphthoic acid derivatives. Naphthoic acid derivatives such as, 6-[3-(1-adamantyl)-4-methoxyphenyl]-2-naphthoic acid, which is commonly called adapalene (the product Differine® sold by Galderma), are widely described and recognized as active ingredients that are just as effective as tretinoin for the treatment of acne. Ioannides D., Rigopoulos D. and Katsambas A., 2002. Topical adapalene gel 0.1% vs. isotretinoin gel 0.05% in the treatment of acne vulgaris: a randomized open-label clinical trial [Br J Dermatol. Sep;147(3):523-7].

Some Adverse Events appear with Rx products (mainly retinoids topical/oral) produce important related AE and frequent cutaneous side effects such as Ziana: 27% subjects with related application site AE and the most important is dry skin.

Skin Care regimen recommended by dermatologists for acne treatment encompasses the following steps:
Step 1: Wash
Step 2: Medicate (Rx treatment)
Step 3: Hydrate & Protect It is useful to have Skin Care Products which improve Acne Signs/Symptoms.

It is well established that Rx treatments are efficient. However, there is a need for new well-tolerated topical pharmaceutical compositions, which have both properties of treating, improving quality of skin, and washing the skin, preferably of acne patients. Consequently, step 2 of medicating is optional according to the present invention or can be considered automatically fulfilled by using the benzoyl peroxide (BPO) in the composition.

The present invention provides topical dermatological/pharmaceutical composition and particularly provides stable and well-tolerated BPO wash composition.

The effectiveness of the BPO is linked to its decomposition when it is brought into contact with the skin. It is the oxidizing properties of the free radicals produced during this decomposition which produces the desired effect. Thus, in order to maintain optimum effectiveness for the benzoyl peroxide, it is important to prevent its decomposition before use, i.e. during storage.

BPO is a chemical compound that is unstable and that reacts with a large array of raw materials especially surfactants and oils. This inherent instability makes BPO difficult to formulate in finished products, especially wash compositions that contain surfactants for the benefit of their cleansing and foaming properties.

The inventors have also observed that well known surfactants are incompatible with BPO and result in less stable compositions. Classical surfactants with cleansing properties are also known to be irritating to the skin.

In one embodiment, the present invention provides composition with the aim of reducing adverse events secondary to acne treatments i.e. dry skin; erythema; stinging/burning.

BPO wash products already exist in the market; however, many are not well stabilized. Several products use amphoteric surfactants, which have been shown to destabilize BPO. There is consequently a risk that these compositions may be less chemically stable. Some of these products indicate on the packaging that the product needs to be vigorously shaken before use. This indicates that the composition, and/or the BPO suspensions undergo sedimentation and are therefore exhibit a form of physically instability, Additionally some of these products use such high concentrations of BPO, and/or some surfactants that exacerbate irritation associated with acne treatment. The irritant effect of various products is highlighted by the opinion of some patients. Several of these products do possess optimal foaming properties as preferred by patients. These limitations impact patience compliance and ultimately effectiveness of acne treatment Foaming properties are generally not compatible with emulsions as most emulsifiers that are required to form the emulsion (i.e. emulsify the internal phase of the emulsion in the external or continuous phase), inhibit foam formation i.e. they are foam breakers. Consequently, it is very challenging to produce an emulsion-based BPO wash with the required level of physical and chemical stability and appropriate level of foaming properties. Nevertheless it is conceivable that emulsion-based BPO wash emulsions may offer more cosmetically appealing formulations than gel-based BPO wash formulations. Emolliency, skin feel and spreadability and other organoleptic properties are well-known advantages of emulsions; however they can present stability challenges that gels may not e.g. phase separation.

There is consequently a need for a non-irritating BPO Wash emulsion. In a specific embodiment, the present invention provides a BPO wash composition, preferably in an emulsion-based wash form with desirable tolerance, stability foaming properties.

The patentee has discovered that this need could be met using, in the same composition, at least one specific surfactant, Zinc gluconate, a salt or derivative of Glycyrrhizic acid or glycyrrhetinic acid and suitable emulsifier(s) to obtain emulsion-based wash containing BPO with appropriate chemical and physical stability.

Thus one aspect of the present invention is a composition, which is a topical wash emulsion comprising:
 a) Benzoyl peroxide (BPO)
 b) At least one mild surfactant with cleaning and/or foaming properties compatible with BPO selected from anionic and/or non-ionic surfactant classes
 c) Zinc gluconate
 d) Dipotassium glycyrrhizate
 e) An oily phase
 f) At least one non-ionic emulsifier from the family of sugar ester derivatives, and/or polyglycerol esters and/or gemini surfactants.

The composition includes benzoyl peroxide (BPO).

BPO can be solubilized or dispersed in the composition. In a specific embodiment of the invention, the benzoyl peroxide is in dispersed form in the composition. By dispersed form according to the invention, BPO is considered to be maintaining in stable suspension in the composition. Alternatively, the benzoyl peroxide is encapsulated (with the exception of encapsulation technology described in the patent U.S. Pat. No. 7,758,888) or adsorbed or absorbed/coated onto a support or free form.

For example—BPO may be encapsulated in a polymer system consisting of porous microspheres, such as microsponges sold under the name of Benzoyl peroxide MICRO-SPONGE P009A by Cardinal Health or an Allyl Metacrylates Crosspolymer such as Poly-Pore sold under the name Poly-Pore 438BP/Benzoyl Peroxide by Amcol HBS.

Preferably, the composition comprises between 0.5% and 10% w/w of BPO, preferentially between 1% w/w and 15% w/w preferred between 2.5% w/w and 3.5% w/w. Percent weight in weight (% w/w) is expressed by weight of active ingredient relative to the total weight of the composition The patentee has noted that chemical stability of BPO is more difficult to achieve with relatively low concentrations of BPO (e.g. <5% w/w BPO) than for higher concentrations. However, due to the requirement of Low-irritancy and high tolerability, the composition of the invention should contain a concentration of BPO preferably not above 3.5%. This low concentration leads to additional difficulties to ensure acceptable BPO stability in the composition over time.

The inventors have observed that most of well-known surfactants are incompatible with the BPO and this resulted less stable compositions.

Specifically, it was also found that the chemical stability of a composition comprising BPO was greatly improved when specific kinds of surfactant were utilized. Indeed, considering the large panel of surfactants such as amphoteric surfactants, non-ionic, anionic surfactants or cationic surfactants, it has been shown in the examples that only certain anionic surfactants and non-ionic surfactants can provide stable compositions with BPO for purposes of the instant invention.

Therefore, in one embodiment, the present invention provides compositions with new generation of very mild anionic and/or non-ionic surfactants with cleaning and/or foaming properties that are adapted to acne and sensitive skin and are compatible with BPO and with an emulsion-based wash composition.

Surfactants are considered to be mild when their application results in minimal swelling, binding and irritation of the skin. Sodium Lauryl sulphate (SLS) is often selected as a reference example of an irritating surfactant. A mild surfactant is less irritant than Sodium Lauryl sulfate but also Sodium lauryl ether sulfate. In general, Sodium lauryl ether sulphate is considered as a less irritating anionic surfactant than SLS.

The first category of surfactants are mild surfactants having detergent, cleansing and/or foaming properties selected from anionic and/or non-ionic surfactants and more specifically selected from the following list, used alone or in combination.

An anionic surfactant is designated as such due to the presence of a negatively charged ion of the molecule. The general form of an anionic surfactant is $RX^-M^+$, where R is the carbon chain length, M is the neutralizing group (such as sodium, potassium, magnesium, zinc, ammonium triethanolamine . . . ), X is the negatively charged species which can be any of the following: carboxylate, sulfonate, sulfate or phosphate.

These surfactants possess desirable foaming and detergent and/or cleansing properties. The mild anionic surfactants are more specifically selected from the following list, used alone or in combination:
 Carboxylate derivatives
  alkyl Isethionates or acyl isethionates (salts of sodium, potassium, ammonium or magnesium) like sodium cocoyl isethionate sold by clariant with the trade name Hostapon SCI-85G or sodium lauroyl methyl isethionate called Iselux from Innospec, Amino acids and Acyl amino acids such as glutamate, acyl glutamate : sodium lauroyl glutamate called Protelan AGL 95 sold by Zschimmer & Schartz, sodium capryloyl glutamate also sold by Zschimmer and Schartz and called Protelan AG8, sarcosinate or acyl sarcosinate such as sodium lauroyl sarcosinate called Protelan LS9011 sold by Zschimmer & Schartz, glycinate or acyl glycinate such as cocoyl glycinate called Hostapon SG from Clariant, fatty acid arginate, alaninate or acyl alaminate, acyl peptides, Cocoyl Apple Amino Acids such as Proteol APL from SEPPIC, lactylates or acyl lactylates, sodium lauryl glucose carboxylate (plantapon LGC Sorb from Cognis), sodium laureth-13 carboxylate.
 Sulfate derivatives:
  Alkyl sulfates, alkylamido ether sulfates, alkylarylpolyether sulfates, monoglyceride sulfates, alkyl ether sulfates such as Zinc coceth sulfate sold by Zschimmer & Schartz with the trade name Zetesol ZN.
 Sulfonate derivatives:
  alkyl sulfonates, alkylamidesulfonates, alkylaryl, $\alpha$-olefinsulfonates and preferentially $C_{14}$-$C_{16}$ $\alpha$-olefinsulfonates preferably its sodium salt such as Hostapur OSB, Hostapur OS Liq from Clariant, or Nansa LSS 495H from Hunstman or Bioterge AS-90 Beads from Stephan, paraffinsulfonates, alkyl sulfosuccinates such as Dioctyl sodium sulfosuccinate also known under the name sodium docusate, alkyl ether sulfosuccinates, alkylamidesulfosuccinates; alkyl sulfoacetates; Alkyl taurates or Acyl taurate such as fatty acid methyl taurate, sodium methyl cocoyl taurate sold by Seppic with the trade name Somepon T25.

Phosphate derivatives:
  alkyl ether phosphates, alkyl phosphates

Examples of non-ionic foaming surfactants, one can mentions the following:
  alkyl polyglucosides such as cocoglucoside (Plantacare 818 from Cognis), decyl glucoside (Plantacare 2000 from Cognis), lauryl glucoside (Plantacare 1200 from Cognis), caprylyl/capryl glucoside (Oramix CG110 from Seppic).
  alkoylated alcohols such as PEG-40 glyceryl cocoate, glyceryl esters and ethers of sorbitan such as PEG-80 sorbitan laurate (Tween 28 sold by Cognis).
  sugar esters such as sucrose laurate, sucrose stearate or sucrose palmitate.

In a preferred embodiment, the present invention provides compositions with new generation of very mild cleansing and/or foaming surfactants adapted to acne and sensitive skin compatible with BPO and selected from the following to be used alone or in combination: zinc coceth sulfate, sodium cocoyl isethionate, sodium lauroyl methyl isethionate, $C_{14}$-$C_{16}$ α-olefinsulfonates preferably its sodium salt and alkyl polyglucoside more preferably decyl glucoside.

Accordingly, the anionic and/or non-ionic surfactants have a concentration between 0.2% w/w and 20% w/w expressed by weight of active material (% w/w AM) relative to the total weight of the composition, preferably between 0.25% w/w and 10% w/w, and more preferably between 0.5% w/w and 5% w/w.

Active material refers to the percentage of pure surfactant included in a formulation. In many cases commercially available surfactants are sold as aqueous solutions. The amount of AM can vary upon the amount of water used to dilute the neat surfactant and the grade of raw material supplied from commercial vendors.

In the composition according to the invention, one skilled in the art will therefore adapt the right concentration of the commercial surfactant to be used in the composition to reach the required concentration preferably between 0.5% and 5% of active material relative to the total weight of the composition.

According to the invention, the composition comprises also Zinc gluconate. Zinc gluconate (also called *zincum gluconium*) is the zinc salt of Gluconic acid. It is an ionic compound consisting of two moles of Gluconate for one mole of zinc. Zinc gluconate is a popular form for the delivery of zinc as a dietary supplement.

Gluconic acid is found naturally, and is industrially manufactured by the fermentation of glucose, typically by *Aspergillus niger*, but also by other fungi, e.g. *Penicillium*, or by bacteria, e.g. *Acetobacter, Pseudomonas* and *Gluconobacter*. In its pure form, it is a white to off-white powder. It can also be manufactured by electrolytic oxidation, although this is a more expensive process. The advantages are a lower microbiological profile, and a more complete reaction, yielding a product with a longer shelf life.

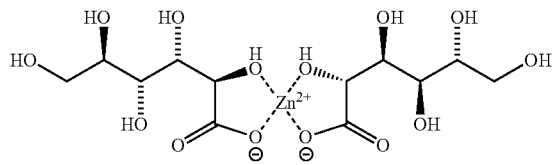

In a preferred embodiment, the concentration of Zinc gluconate expressed by weight relative to the total weight of the composition is between 0.1 and 1%, preferably between 0.15 and 0.3, more preferably 0.2%

According to the invention, the composition also contains a salt or derivative of Glycyrrhizic acid or of Glycyrrhetinic acid.

Glycyrrhizic acid is derived from the plant Glycyrrhiza glabra, or liquorice root, it is reputed to provide anti-irritant and anti-inflammatory properties. The soothing and calming properties of Liquorice extracts make them interesting candidates for inclusion in treatments for sensitive skin conditions such as eczemas, erhythema, seborric dermatitis and itching.

Glycyrrhetinic acid is a pentacyclic triterpenoid derivative of the beta-amyrin type obtained from the hydrolysis of glycyrrhizic acid (alternative names: Glycyrrhizin or Glycyrrhizinic acid), obtained from the herb liquorice. It is used in flavoring and it masks the bitter taste of drugs like aloe and quinine. It is effective in the treatment of peptic ulcer and also has expectorant (antitussive) properties. It has some additional pharmacological properties including anti-viral, antifungal, antiprotozoal, and antibacterial activities

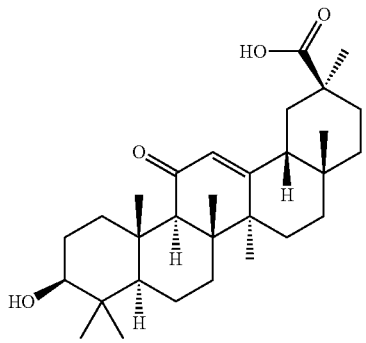

Chemical structure of Glycyrrhetinic acid

As Glycyrrhriziate salts and derivatives, can cite potassium salt, sodium salt, monoammonium salt can be cited as examples. As Glyccyrrhizic acid salts and derivatives the following can be cited as examples: succinate, disodium, dipotassium salts of or esters of said acid such as glycerin monoester.

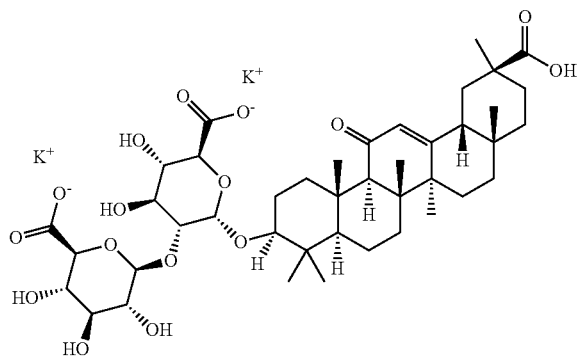

Chemical structure of Dipotassium Glycyrrhizate

In a preferred embodiment, the Glycyrrhetinic derivative is Dipotassium glycyrrhizate is utilized at a concentration expressed by weight relative to the total weight of the composition between 0.1 and 1%, preferably between 0.15 and 0.3%, more preferably 0.25%.

The composition is for topical application. Preferably, the composition is in the form of an oily dispersion into an hydrophilic phase, aqueous or aqueous alcoholic medium, dispersion of lotion type, emulsion of liquid or semi-liquid consistency of milk type, obtained by dispersion of a fatty phase in an aqueous phase (O/W) or suspensions or emulsions of soft, semi-liquid or solid consistency of the cream, gel, cream-gel, foam or ointment type, or microemulsions, microcapsules, microparticles or vesicular dispersions of ionic and/or nonionic type, in the form of sprays, or else in the form of dermal devices such as patches.

In a specific embodiment, the composition according to the invention is in a form of an emulsion-based wash. An emulsion can be defined as a system comprising two immiscible phases, and in which one phase is dispersed into the other and generally stabilized by a surfactant. Preferably, the emulsions used include at least one emulsifier, a hydrophilic phase, preferably aqueous, and apolar or nonpolar fatty phase. Preferably, they are in the form of an oil in water emulsion (O/W).

An emulsion is called a lotion when its viscosity is low and is pourable. Lipophilic creams are water-in-oil emulsion (W/O); hydrophilic creams are oil in water emulsions (O/W).

In a preferred embodiment, the composition of the invention is an oil in water emulsion, containing an aqueous phase with at least 5% water by weight of total composition, preferably between 5 and 90%, more preferably between 50 and 90%. The hydrophilic phase of the emulsion of the invention is preferably aqueous, and may thus comprise water. This water can be purified water, floral water such as cornflower water, or a natural spring or mineral water, for example selected from water from Vittel, waters from the Vichy basin, water from Uriage, the water from La Roche Posay, Avene water or water from Aix les Bains.

In an optional embodiment of the invention, the aqueous phase can also contain a polyol (triol at mininum) preferably selected from the group of trihydric alcohols (such as glycerol or glycerin), tetrahedral (as diglycerol) or hexahydric (such as sorbitol). The amount of polyol of the invention is between 0,1 and 40% by weight relative to the total weight of the composition.

In a preferred embodiment, the composition of the invention contains glycerin in an amount between 0.1 and 10% and water in an amount between 50% and 90% by weight of total composition.

Accordingly, the oil in water emulsion according to the invention comprises a fatty phase.

This fatty phase may comprise, for example, vegetable oils, mineral, animal or synthetic oils, silicones, and mixtures thereof.

Examples of mineral oil can include paraffin oils of various viscosities such as those sold by Esso, Marcol 152 ®, Marcol 82® and Primol 352®. Examples of vegetable oil include almond oil, palm oil, soybean oil, sesame oil, or sunflower oil.

Examples of animal-sourced oil include lanolin, squalene, fish oil, mink oil. Squalane is sold under the trade name Cosbiol® by Laserson company. Synthetic oils may include esters such as Cetearyl isononanoate as the product sold by Cognis under the trade name Cetiol SN PH® , isopropyl palmitate or isopropyl myristate sold respectively under the names Crodamol IPP ® and Crodamol IPM® by Croda, diisopropyl adipate also sold by Croda under the name Crodamol DA®, and caprylic/capric triglyceride such as Miglyol 812® sold by Univar or also hydrogenated polyisobutene such as parleam® sold by Rossow company.

Examples of volatile silicone oils include the product sold under the name ST-Cyclomethicone 5-NF® by Dow Corning. Non-volatile silicones include dimethicone as the products sold under the name Q7-9120 silicone fluid with a viscosity of 20 cst to 12500 cst Solid fat such as natural or synthetic waxes, fatty acids such as stearic acid, fatty alcohols such as Speziol C18 pharma® sold by Cognis, and texturizing agents such as tribehenate type, called Compritol 888® (sold by Gattefosse) or hydrogenated castor oils such as Cutina HR® sold by Cognis can be added in the composition. In this case, one skilled in the art will adjust the heating temperature of the preparation in relation to the presence or absence of these solids. Shea butter such as lipex 102® or lipex 202® from AAK company can also be used.

However, the inventors have observed that chemical stability of BPO and physical stability of the composition of the invention are observed with only limited lists of oily phase. Accordingly, the oily phase of the invention comprises preferably mineral oil, synthetic oils and silicone oils alone or in combination.

Paraffin oils, hydrogenated polyisobutene, or mixtures of silicones, such as cyclometicones and dimethicone are particularly preferred.

In a preferred embodiment the quantity of fatty phase is selected between 1% and 15%, more preferably between 0.5% and 10%.

Throughout the present text, unless otherwise specified, it is understood that, when concentration ranges are given, they include the upper and lower limits of said range. Similarly, unless otherwise indicated, the proportions of the various constituents of the composition are expressed as percentage by weight (w/w) of the total weight of said composition.

The wash emulsion according to the invention comprises specific surfactants/emulsifiers in order to maintain stable dispersion of the oily phase into the aqueous phase. To perform the stable emulsion according to the invention, these surfactants can be selected from the following list:

surfactant derived from sugar such as sucrosesters,
polyglycerol esters,
Gemini surfactants.

Sucrosesters are nonionic surfactants having a hydrophilic group formed by the sucrose part and a lipophilic group which comprises a fatty acid. Said sucrose generally having a total of 8 hydroxyl groups, it is possible to obtain esters of sucrose ranging from a "mono" sucrosester to a "Octa" sucrosester. Non-limitating examples of sucrosesters include sucrose stearate, sucrose laurate or sucrose palmitate sold under the trade name SURFHOPE by MITSUBISHI KAGAKU that are the preferred esters of sucrose in the composition of the invention. The composition may also include mixtures such as Sucragel CF and Sucragel AOF containing sucrose laurate or the mixture Sucragel AP containing sucrose laurate and sucrose myristate or also the mixture of Sucrablend SP containing sucrose palmitate and sucrose stearate sold by ALFA Chemicals Limited. Surfhope and Sucragel surfactants are particularly preferred.

In another embodiment of the invention the surfactants used are esters of polyglycerol. These materials are comprised of Polyglycerin fatty acid esters that are obtained by condensation of fatty acids with glycerin. Example include: Ryoto polyglyvrol esters ER-60D, ER-30D or S-FACE surfactants from SAKAMATO, decaglycerol monomyristate sold under sold the name S-FACE M-1001 and decaglycerol monolaurate called S-FACE L-1001 sold by Sakamoto company.

Alternatively, Gemini surfactants can be used. Gemini surfactants consist of two conventional surfactant molecules chemically bonded together by a spacer such as acyl-L-glutamate. Gemini surfactants, sometimes called dimeric surfactants, have hydrophilic head groups and two hydrophobic tails in contrast to conventional surfactants that generally have a single hydrophilic head group and a single hydrophobic tail. Gemini surfactants can be from ten to hundred times more surface-active than conventional surfactants with similar single hydrophilic and purpose group. In the hydrophobic tail, Gemini surfactants have remarkably low CMC (critical micellar concentration) values compared to the corresponding conventional surfactants of equivalent chain length. The bi-layer structure of the Gemini surfactant makes it compatible with ceramides and skin providing skin barrier properties. Gemini surfactants have even been reported in literature to reduce skin irritation. Examples include: sodium dilauramidoglutamide lysine sold by Asahi Kasei Group under the trade name Pellicer L-30 or Pellicer LB-10. The Gemini surfactant may be used, for example, in mixture with other surfactants such as the products sold by the Sasol company under the trade name Ceralution ®, and especially the following products:

CERALUTION C®: Aqua (Water), Caprylic/Capric Triglyceride, Glycerin, Ceteareth-25, Disodium Ethylene Dicocamide PEG-15 Disulfate, Sodium Lauroyl Lactylate, Behenyl Alcohol, Glyceryl Stearate, Glyceryl Stearate Citrate, Xanthan Gum CERALUTION H®: Behenyl Alcohol (and) Glyceryl Stearate (and) Glyceryl Stearate Citrate (and) Disodium Ethylene Dicocamide PEG-15 Disulfate CERALUTION® F: Sodium Lauroyl Lactylate, Disodium Ethylene Dicocamide PEG-15 Disulfate The preferred surfactants are sucroses esters and more preferably the Surfhope and Sucragel products or the Gemini Surfactants, such as the Pellicer.

The emulsifiers of the invention are used between 0.01% and 7% by weight relative to the total weight of the composition, preferably between 0.1 and 5%.

The composition according to the invention may also in particular comprise at least one "gelling agent" or "suspending agent".

The term "gelling agent" or "suspending agent" is intended to mean an agent capable of maintaining the benzoyl peroxide in suspension, even under the influence of a variation in pH due to the release of benzoic acid by the benzoyl peroxide. The gelling agent or the suspending agent" according to the invention also:

Imparts appropriate physical stability, i.e. no decrease in viscosity is observed over time at temperatures between 4 and 40° C.

Maintainins appropriate chemical stability of the active agents, i.e. no degradation of the active agents is observed over time and at temperatures between 4 and 40° C.

By way of non-limiting examples of "gelling agents" or "suspending agents" that can be part of the compositions according to the invention alone or as mixtures, mention may be made of the microcrystalline cellulose and sodium carboxymethyl cellulose (such as this sold as Avicel CL-611 or RC-S91 by FMC Biopolymer company), the "electrolyte-insensitive" carbomers sold under the name Ultrez 20™, Carbopol 1382™, acrylates/C10-30 Alkyl crosspolymer sold under the name Pemulen TR1, Pemulen TR2 or Carbopol ETD2020™ by the company Noveon; polysaccharides, non-limiting examples of which include xanthan gum, such as Xantural 180™ sold by the company Kelco, or gellan gum for example Kelcogel High acyl or low acyl such as Kelcogel F or also a pectin such as Genu pHresh sold by KELCO, the family of magnesium aluminium silicate such as Veegum K™ or Veegum Ultra sold by the company Vanderbilt Minerals LLC, Sodium magnesium silicate, Sodium magnesium fluorosilicate, Magnesium Sodium Silicate and Tetrasodium pyrophosphate sold under the trade name Laponite, by Rockwood company, Guar gum such as Jaguar products from Rhodia, Chitosans, Cellulose and its derivatives such as hydroxypropyl methylcellulose, in particular the product sold under the name Methocel E4 premium™ by the company Dow Chemical or hydroxyethyl-cellulose, in particular the product sold under the name Natrosol HHX 250™ by the company Aqualon, or Sodium carboxymethyl cellulose such as Blanose from Ashland, the family of carrageenans in particular those in the four following sub families: κ, λ, β, ω such as Viscarin ® or Gelcarins ® sold by the company IMCD, the family of clay minerals more precisely smectite group suxh as dioctatedral smectite (bentonite) for example, the family of acrylic polymers associated with hydrophobic chains such as the PEG-150/decyl/SMDI copolymer sold under the name Aculyn 44™ (polycondensate comprising at least, as elements, a polyethylene glycol comprising 150 or 180 mol of ethylene oxide, decyl alcohol and methylene-bis(4-cyclohexylisocyanate) (SMDI), at 35% by weight in a mixture of propylene glycol [39%] and water [26%]), acrylates/steareth-20 methacrylate crosspolymer, sold under name ACULYN 88, acrylates/steareth-20 methacrylate copolymer sold under trade name ACULYN 22 BY Rhom and Haas, acrylates copolymer sold under names Aqua SF1 by Noveon-Lubrizol, polyacrylate-1 crosspolymer (Aqua CC by Noveon), Acrylates crosspolymer 4 (Aqua SF2 by Noveon) or acrylates/Beheneth-25 Methacrylate copolymer sold under trade name Novethix L-10, polyacrylate-13 & Polyisobutene & Polysorbate 20 sold under the name SEPIPLUS 400 by the company Seppic, and the gelling agent of the polyacrylamide family such as sodium acryloyldimethyltaurate copolymer/isohexadecane/polysorbate 80 mixture sold under the name Simulgel 600PHA™ by the company Seppic, or the polyacrylamide/isoparaffin C13-14/laureth-7 mixture such as, for example, that sold under the name Sepigel 305™ by the company Seppic, by the Hydroxyethyl Acrylate/Sodium Acryloyl dimethyl Taurate Copolymer under the name SEPINOV EMT 10 by the company Seppic and the family of modified starches such as the modified potato starch sold under the name Structure Solanace™, or else mixtures thereof.

The gelling agent can also be a neutralized polymeric sulfonic acid such as Ammonium Acryloyl dimethyltaureate/carboxyethyl acrylate crosspolymer sold by the company Clariant under the trade name ARISTOFLEX TAC.

The preferred gelling agents are derived from the acrylic polymer family or "electrolyte-insensitive" carbomers such as Carbopol 1382™ or Carbopol ETD2020, polysaccharides family such as xanthan gum or pectin, cellulose derivatives such as hydroxypropyl methylcellulose or hydroxyethylcellulose;,and Bentonite such as Polargel HV from Americain colloid Company or Optigel CK from Rockwood and magnesium aluminium silicates such as Veegum K and Veegum ultra and neutralized polymeric sulfonic acid polymers such as Ammonium Acryloyl dimethyltaureate/carboxyethyl acrylate crosspolymer used alone or as a mixture. More preferably, in the gel composition according to the invention, the gelling agent is magnesium silicates such as Veegum K and Veegum Ultra and/or xanthan gum.

The gelling agent as described above can be used at the preferential concentrations ranging from 0.001% to 15% and more preferentially between 0.15% and 7%.

The composition according to the invention may also in particular comprise at least one wetting agent. The wetting capacity is the tendency of a liquid to spread out over a surface.

Preferably, they are wetting agents which have an HLB (hydrophilic/lipophilic balance) of 7 to 18, or nonionic wetting agents of polyoxyethylenated and/or polyoxypropylenated copolymer type or anionic wetting agent such as sodium docusate. As non limited examples of wetting agents, mention can be made of Poloxamers and more particularly the product as known as SYNPERONIC® PE/L44 and/or SYNPERONIC® PE/L62 sold by Croda (formerly Uniqema), glycols such as those known as propylene glycol, dipropylene glycol, lauroglycol, propylene glycol dipelargonate, ethoxydiglycol. They should be liquid to facilitate ready incorporation into the composition without the need for heating.

Among the wetting agents, whose role it is to reduce the surface tension and to allow greater spreading of the liquid over the surface of solid particles, use is preferentially made, without this list being limiting, of compounds such as those of the poloxamers and/or glycols families and more particularly SYNPERONIC® PE/L44 and/or SYNPERONIC® PE/L62 and/or compounds such as propylene glycol, dipropylene glycol, propylene glycol dipelargonate, lauroglycol, ethoxydiglycol and sodium docusate.

By way of preferred wetting agent, mention may be made of propylene glycol or SYNPERONIC® PE/L44 (Poloxamer 124).

The concentration of wetting agents used in the compositions according to the invention is between 0.001% and 20%, preferentially between 0.1% and 10% and more preferably between 1 to 7% in weight with regards to the total composition weight.

The term "topical application" is intended to mean application to the skin or the mucous membranes.

The composition according to the invention may further comprise at least one of the following additives mentioned as an example, used in the composition alone or in combination:

Antioxidants such as vitamin E and its derivatives, such as DL alpha tocopherol or tocopherol acetate from Roche, vitamin C and its derivatives, as Ascorbyl Palmitate Roche, Butylated hydroxytoluene sold under the name Nipanox BHT by Clariant, sodium metabisulfite, vitamins such as vitamin PP or niacinamide, Soothing agents and/or anti-irritants such as PPG-12/SMDI copolymer marketed by Bertek Pharmaceuticals under the trade name Polyolprepolymer-2 or allantoin or its derivatives, or hyaluronic acid, Polyquaternium-51 such as lipidure PMB sold by Rossow, D-panthenol, aloe vera, Lecithins, Cholesterol, Preservatives: such as benzalkonium chloride, bronopol, chlorhexidine, chlorocresol and its derivatives, ethyl alcohol, phenoxyethanol, potassium sorbate, sodium benzoate diazolidinylurea, benzyl alcohol, parabens or mixtures thereof methyl paraben sold under the name Nipagin M by Clariant, Propyl paraben sold under the name Nipasol by Clariant or mixture of them sold under the trade name Nipastat by Clariant, Acids or bases such as citric acid, lactic acid, anisic acid, sodium citrate, triethanolamine, aminomethyl propanol, sodium hydroxide, diisopropanolamine, Chelating agents such as EDTA and its salts such as Disodium EDTA, Humectant agents such as propylene glycol, glycerin, pentylene glyco1,1-2 hexanediol or caprylyl glycol, propane-1,3-diol, Foam boosters selected, for example, from polyethylene glycol such as PEG-75, or glycerylmonocaprylate (Imwitor 308 from Sasol), sorbitan sesquicaprylate (Antil soft SC from Evonik) used in the composition alone or in combination.

Ingredients providing smoothness to the foam, selected from PEG-7 glyceryl cocoate, PEG 200 hydrogenated glyceryl palmate (Antil 200 from Evonik), Polypropylene Terephtalate (Aristoflex PEA from Clariant), C12-13 Alkyl Lactate (Cosmacol ELI from Sasol) and used in the composition alone or in combination.

Perfume solubilising agent such as PEG-40 hydrogenated castor oil, PEG-60 hydrogenated castor oil, polysorbate 80, polysorbate 20, used alone or in combination.

Perfume or ingredients providing fragrance to the composition such as natural or essential oils.

Refatting agents such as Lamesoft PO 65 from Cognis (cocoglucoside and glyceryl oleate), softigen 767 (PEG-6-Caprylic/Capric Glycerides) from Sasol.

In a preferred embodiment, the composition according to the invention is a topical wash composition comprising:

a) Benzoyl peroxide (BPO),
b) At least one anionic and/or non-ionic surfactants, selected from Zinc coceth sulfate; sodium cocoyl isethionate, sodium lauroyl isethionate, C14-C16 α-olefinsulfonates preferably its sodium salt and decyl glucoside,
c) Zinc gluconate
d) Dipotassium glycyrrhizate
e) An oily phase
f) An aqueous phase,
g) At least one non-ionic emulsifier from the family of sugar ester derivatives, and/or polyglycerol esters and/or gemini surfactants.

According to a preferred embodiment, the wash composition is a foaming composition.

According to a further preferred embodiment, the composition is an oil in water emulsion.

More preferably the topical wash composition comprises:

a. Between 1% w/w and 5% w/w of benzoyl peroxide
b. Between 0.5% w/w and 5% w/w expressed by weight of active material relative to the total weight of the composition of at least one anionic and/or non-ionic surfactants selected from Zinc coceth sulfate, sodium cocoyl isethionate, sodium lauroyl methyl isethionate, C14-C16 α-olefinsulfonates and decyl glucoside, in a total concentration
c. Between 0.1 w/w and 1%w/w of Zinc gluconate
d. Between 0.1 w/w and 1%w/w of Dipotassium glycyrrhizate.
e. Between 1 and 15% of an oily phase,
f. Between 5 and 90% of an aqueous phase
g. Between 0.1 and 5% of sugar ester derivatives, and/or polyglycerol esters and/or gemini surfactants.

The present invention further concerns a composition as defined herein, for its use for improving and/or preventing and/or inhibiting dermatological conditions linked to acne as defined hereafter.

According to a preferred embodiment, the invention concerns such a composition for its use for preventing, inhibiting or treating common acne.

Another subject of the present invention is the use of a composition according to the invention, for the treatment and/or prevention of dermatological conditions linked to acne treatment and particularly common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne and acne medicamentosa. Preferably, the preparation of a pharmaceutical composition is intended for use in preventing, inhibiting or treating common acne.

The invention also provides a method for improving and/or preventing and/or inhibiting dermatological conditions linked to acne treatment. The invention provide also a treatment process for embellishing the skin or its surface appearance, in which a composition comprising, in a physiologically acceptable medium, a retinoid, an anti-irritant and BPO is applied to the skin and/or its integument annexes. In a preferred embodiment, the treatment of skin is for skin with an acneic tendency or for combating the greasy appearance of the skin or the hair.

Throughout the present text, unless otherwise specified, it is understood that, when concentration ranges are given, they include the upper and lower limits of said range. Similarly, unless otherwise indicated, the proportions of the various constituents of the composition are expressed as percentage by weight (w/w) of the total weight of said composition.

One problem answered by the composition of the invention is the stability of foaming wash composition containing BPO. Stability encompasses chemical and physical stability.

Compositions are considered physically stable if its organoleptic characteristics, pH, viscosity and homogeneity of BPO dispersion remain within defined parameters over time at various storage temperatures (4° C., room temperature, 30° C. and 40° C.). According to the invention, room temperature is considered a temperature comprised between 15° C. and 25° C.

Compositions are considered chemically stable if the active drug concentration remains within defined parameters over time at various storage temperatures e.g. 4° C., room temperature, 30° C. and 40° C. Consequently, the active drug is present in the composition at an acceptable percentage versus the initial amount incorporated into the formulation.

According to the invention, compositions are considered chemically stable when the BPO content is within 90 to 110% of the targeted active drug substance concentration.

The present invention will now be illustrated by means of the following examples, which cannot limit the scope of the present invention.

The following examples describe various formulations according to the invention. Stability has been analysed by:

Measurement of remaining BPO over time at various temperatures in order to determine the chemical stability of the BPO. Analysis was performed using high pressure liquid chromatography (HPLC) with Ultraviolet (UV) detection at 235 nm. The concentration of BPO in each example (either mixture or formulation) is expressed as a percentage of the initial amount.

Physical analysis of the composition to observe the BPO suspension and to assess any sedimentation or agglomeration. Additionally, pH and viscosity measurements and organoleptic evaluation were performed as part of the physical analysis.

As a general observation, all compositions according to the according to the invention (with the exception of example 1) according and demonstrated by the following examples have demonstrated acceptable physical stability with no modification of the BPO suspension.

The present invention will now be illustrated by means of the following examples, which cannot limit the scope of the present invention.

EXAMPLES

Example 1

Comparative Stability Test to Demonstrate the Chemical Instability of BPO with Classical Amphoteric Surfactants. High Pressure Liquid Chromatography (HPLC) Analysis with UV Detection was Used to Quantify BPO in the Samples Composition containing purified water, BPO and 5% sodium cocoamphoacetate, an amphoteric surfactant, sold under the product name REWOTERIC® AM C by Evonik or AMPHOSOL® 1C from Stepan.

| Composition | % w/w |
| --- | --- |
| Purified water | 92.5 |
| BPO | 2.5 |
| Sodium cocoamphoacetate | 5 |

Chemical stability of BPO in purified water and 5% Sodium cocoamphoacetate after 1 month at 40° C.

| Sampling interval | % BPO (relative to initial value) |
| --- | --- |
| T0 (initial) | 100 |
| T1M (40° C.) | <0.1 |

The results indicate that no BPO was retrieved in the solution after 1 month, thereby demonstrating that all BPO added to the composition during manufacture and assayed at the initial interval (T0) was degraded.

Composition containing purified water, BPO and 5% of disodium cocoamphodiacetate, an amphoteric surfactant sold under the product name REWOTERIC® AM 2 C NM by Evonik.

| Composition | % w/w |
|---|---|
| Purified water | 92.5 |
| BPO | 2.5 |
| Disodium cocoamphoacetate | 5 |

Chemical stability of BPO in purified water and 5% Disodium cocoamphodiacetate after 1 month at 40° C.

| Sampling interval | % BPO (relative to initial value) |
|---|---|
| T0 (initial) | 100 |
| T1M (40° C.) | <0.1 |

The results indicate that no BPO was retrieved in the solution after 1 month, thereby demonstrating that all BPO added to the composition during manufacture and assayed at the initial interval (T0) was degraded.

Example 2

Chemical Stability of BPO with Mild Anionic and Non-Ionic Surfactants.

Composition containing purified water, BPO and 5% of sugar ester (sucrose laurate) from the non-ionic group of surfactants.

| Composition | % w/w |
|---|---|
| Purified water | 92.5 |
| BPO | 2.5 |
| sucrose laurate | 5 |

Chemical stability of BPO in purified water and 5% of sugar ester (Sucrose laurate) after storage for 2 months (T2M) at 40° C.

| Sampling interval | % BPO (relative to initial value) |
|---|---|
| T0 (initial) | 100 |
| T1M (40° C.) | 100.0 |
| T2M (40° C.) | 99.6 |

The results indicate that BPO is stable (assay values between 90-110% of target) in purified water and 5% Sucrose laurate after 2 months storage at 40° C.

Composition containing purified water, BPO and 5% of Decyl glucoside (non-ionic surfactant).

| Composition | % w/w |
|---|---|
| Purified water | 92.5 |
| BPO | 2.5 |
| Decyl glucoside | 5 |

Chemical stability of BPO in purified water and 5% Decyl glucoside after 2 months storage at 40° C.

| Sampling interval | % BPO (relative to initial value) |
|---|---|
| T0 (initial) | 100 |
| T1M (40° C.) | 96.1 |
| T2M (40° C.) | 97.4 |

The results indicate that BPO is stable in purified water and 5% of Decyl glucoside after storage for 2 months at 40° C.

Composition containing purified water, BPO and 5% Zinc coceth sulfate (mild anionic surfactant)

| Composition | % w/w |
|---|---|
| Purified water | 92.5 |
| BPO | 2.5 |
| Zinc coceth sulfate | 5 |

Chemical stability of BPO purified water, BPO and 5% Zinc coceth sulfate after 2 months at 40° C.

| Sampling interval | % BPO (relative to initial value) |
|---|---|
| T0 (initial) | 100 |
| T1M (40° C.) | 94.7 |
| T2M (40° C.) | 97.1 |

The results indicate that BPO is stable in the solution after 2 months at 40° C.

Composition containing purified water, BPO and 5% Sodium cocoyl isethionate (mild anionic surfactant)

| Composition | % w/w |
|---|---|
| Purified water | 92.5 |
| BPO | 2.5 |
| Sodium cocoyl isethionate | 5 |

Chemical stability of BPO in water, BPO and 5% Sodium cocoyl isethionate after storage for 2 months at 40° C.

| Sampling interval | % BPO (relative to initial value) |
|---|---|
| T0 (initial) | 100 |
| T1M (40° C.) | 100.8 |
| T2M (40° C.) | 101.3 |

The results indicate that BPO is stable in a solution of water and 5% Sodium cocoyl isethionate after storage for 2 months at 40° C.

Composition containing purified water, BPO and 5% Sodium methyl cocoyl taurate (mild anionic surfactant).

| Sampling interval | % BPO (relative to initial value) |
|---|---|
| T0 (initial) | 100 |
| T1M (40° C.) | 90.1 |

The results indicate that BPO is stable in a solution of water and 5% Sodium methyl cocoyl taurate after storage for 1 month at 40° C.

For examples 3 to 21, the general manufacturing process was as follows:

Step 1: In the main beaker, weigh the required quantity of purified water and heat to 75° C. before dispersing the Magnesium Aluminium silicate.

Step 2: Cool to 60° C. and add xanthan gum while mixing.

Step 3: Maintain at 60° C. and continue mixing until the gelling agents are hydrated, then add EDTA and foaming surfactants. Mix until homogeneous.

Step 4: Cool to 50° C. and incorporate PEG-75 (as appropriate) and Dipotassium glycyrrhizate while mixing. Mix until homogeneous.

Step 5: Cool to 40° C. and introduce Zinc gluconate and adjust pH with citric acid. Mix until homogeneous.

Step 6: In a secondary beaker, prepare the predispersion of BPO using poloxamer and propylene glycol with high shear maintained at low temperature (with an ice bath).

Step 7: Add the predispersion of BPO in the main beaker while mixing. Continue cooling.

Step 8: Add other additives, as needed (e.g. emulsifying surfactants, oils or perfumes), to the preparation while mixing. Cool to 30° C. and terminate mixing.

All the exemples described below are physically stable after 3 months at RT (room temperature), 30° C. and 40° C.

Example 3

| Composition | % w/w |
| --- | --- |
| Purified water | QSAD 100 |
| Glycerin & caprylic/capric triglycerides & aqua & sucrose laurate | 2 |
| Hydrogenated polyisobutene | 8 |
| magnesium aluminium silicate | 5 |
| Xanthan gum | 0.5 |
| Dipotassium glycyrrhizate | 0.25 |
| Zinc gluconate | 0.2 |
| Zinc coceth sulfate (25% in water) | 8.0 |
| Disodium EDTA | 0.1 |
| Poloxamer 124 | 0.2 |
| Propylene glycol | 2 |
| Phenoxyethanol | 0.8 |
| BPO | 2.6 |
| Citric acid | 0.05 |

Chemical stability of BPO in the composition of example 3 after 3 months of storage at RT and 30° C. and 1 month at 40° C.:

| Storage conditions | Assay values per interval** | | | |
| --- | --- | --- | --- | --- |
| | T0 | T1M | T2M | T3M |
| RT | 100 | 97.6 | 98.2 | 98 |
| 30° C. | — | — | — | 98.9 |
| 40° C. | — | 94.0 | — | — |

**Assay value = percentage of T0.

Data indicated that BPO is chemically stable for 3 months at RT and 30° C. in the formulation as described in example 3.

Example 4

| Composition | % w/w |
| --- | --- |
| Purified water | QSAD 100 |
| Glycerin & caprylic/capric triglycerides & aqua & sucrose laurate | 2 |
| Hydrogenated polyisobutene | 8 |
| Magnesium aluminium silicate | 5 |
| Xanthan gum | 0.5 |
| Dipotassium glycyrrhizate | 0.25 |
| Zinc gluconate | 0.2 |
| Decyl glucoside (55% in water) | 6 |
| Disodium EDTA | 0.1 |
| Poloxamer 124 | 0.2 |
| Propylene glycol | 2 |
| PEG-75 | 2 |
| Phenoxyethanol | 0.8 |
| BPO | 2.6 |
| Citric acid | 0.05 |

Chemical stability of BPO in the composition of example 4 after storage for 3 months at RT and 30° C. and 1 month at 40° C.

| Storage conditions | Assay values per interval** | | | |
| --- | --- | --- | --- | --- |
| | T0 | T1M | T2M | T3M |
| RT | 100 | 98.7 | 95.3 | 111.6 |
| 30° C. | | | | 95.3 |
| 40° C. | | 93.5 | | |

**Assay value = percentage of T0.

Data indicated that BPO is chemically stable for 3 months at RT and 30° C. and 1 month at 40° C. in the formulation as described in example 4.

Example 5

| Composition | % w/w |
| --- | --- |
| Purified water | QSAD 100 |
| Glycerin & caprylic/capric triglycerides & aqua & sucrose laurate | 2 |
| Hydrogenated polyisobutene | 8 |
| Magnesium aluminium silicate | 5 |
| Xanthan gum | 0.5 |
| Sodium lauroyl methyl isethionate (85% purity) | 2.5 |
| Disodium EDTA | 0.1 |
| Poloxamer 124 | 0.2 |
| propylene glycol | 2 |
| PEG-75 | 2 |
| Phenoxyethanol | 0.8 |
| BPO | 2.6 |
| Citric acid | 0.15 |

Chemical stability of BPO in the composition of example 5 after storage for 3 months at RT/30° C. and 2 months at 40° C.:

| Storage conditions | Assay values per interval** | | | |
| --- | --- | --- | --- | --- |
| | T0 | T1M | T2M | T3M |
| RT | 100 | 101.5 | 102.6 | 100.6 |
| 30° C. | | | | 96.7 |
| 40° C. | | 97.4 | 92.8 | |

**Assay value = percentage of T0.

Data indicated that BPO is chemically stable for 3 months at RT and 30° C. and 2 months at 40° C. in the formulation as described in example 5:

Example 6

| Composition | % w/w |
| --- | --- |
| Purified water | QSAD 100 |
| glycerin & caprylic/capric triglycerides & aqua & sucrose laurate | 2 |
| Hydrogenated polyisobutene | 8.0 |
| Magnesium aluminium silicate | 5 |
| Xanthan gum | 0.5 |
| Dipotassium glycyrrhizate | 0.25 |
| Zinc gluconate | 0.2 |
| Sodium C14-C16 olefin sulfate | 2 |
| Disodium EDTA | 0.1 |
| Poloxamer 124 | 0.2 |
| propylene glycol | 2 |
| PEG-75 | 2 |
| Phenoxyethanol | 0.8 |
| BPO | 2.6 |
| Citric acid | 0.15 |
| Fragrance | 0.25 |
| PEG-40 hydrogenated castor oil | 0.25 |

Chemical stability of BPO in the composition of example 7 after storage 3 months at RT and 30° C. and 1 month at 40° C.:

| Storage conditions | Assay values per interval** | | | |
| --- | --- | --- | --- | --- |
| | T0 | T1M** | T2M** | T3M** |
| RT | 100 | 101.2 | 99.9 | 98.1 |
| 30° C. | | | | 94.6 |
| 40° C. | | 97.2 | | |

**Assay value = percentage of T0.

Data indicated that BPO is chemically stable for 3 months at RT and 30° C. and 1 month at 40° C. in the formulation as described in example 6.

Example 7

| Composition | % w/w |
| --- | --- |
| Purified water | QSAD 100 |
| Glycerin& caprylic/capric triglycerides & aqua & sucrose laurate | 2 |
| Glycerin | 4.95 |
| Mineral oil | 8 |
| Magnesium aluminium silicate | 5 |
| Xanthan gum | 0.5 |
| Dipotassium glycyrrhizate | 0.25 |
| Zinc gluconate | 0.2 |
| Sodium C14-C16 olefin sulfonate | 1 |
| Decyl glucoside (55% in water) | 3 |
| Disodium EDTA | 0.1 |
| Poloxamer 124 | 0.2 |
| propylene glycol | 2 |
| PEG-75 | 2 |
| BPO | 2.6 |
| Citric acid | 0.15 |
| Potassium sorbate | 0.1 |
| Benzyl Alcohol | 0.50 |

Example 8

| Composition | % w/w |
| --- | --- |
| Purified water | QSAD 100 |
| Glycerin& caprylic/capric triglycerides & aqua & sucrose laurate | 2 |
| Mineral oil | 1 |
| Dimethicone 350 cst | 7 |
| Ammonium acryloyl dimethyltaurate/ carboxyethyl acrylate crosspolymer | 1.5 |
| Xanthan gum | 0.5 |
| Dipotassium glycyrrhizate | 0.25 |
| Zinc gluconate | 0.2 |
| Sodium methyl lauroyl isethionate (85% purity) | 2.5 |
| Disodium EDTA | 0.1 |
| Poloxamer 124 | 0.2 |
| Propylene glycol | 2 |
| PEG-75 | 2 |
| Phenoxyethanol | 0.8 |
| BPO | 2.6 |
| Citric acid | 0.05 |

Example 9

| Composition | % w/w |
| --- | --- |
| Purified water | QSAD 100 |
| Glycerin & caprylic/capric triglycerides & aqua & sucrose laurate | 2 |
| Hydrogenated polyisobutene | 8 |
| Magnesium aluminium silicate | 5 |
| Xanthan gum | 0.5 |
| Dipotassium glycyrrhizate | 0.25 |
| Zinc gluconate | 0.2 |
| Sodium lauroyl Oat amino acid (32% in water) | 10 |
| Sorbitan sesquicapylate | 0.30 |
| Disodium EDTA | 0.1 |
| Poloxamer 124 | 0.2 |
| Propylene glycol | 2 |
| PEG-75 | 2 |
| Phenoxyethanol | 0.8 |
| BPO | 2.6 |
| Citric acid monohydrated | 0.15 |
| Fragrance | 0.25 |
| PEG-40 hydrogenated castor oil | 0.25 |

Example 10

| Composition | % w/w |
| --- | --- |
| Purified water | QSAD 100 |
| Glycerin& caprylic/capric triglycerides & aqua & sucrose laurate | 2 |
| Hydrogenated polyisobutene | 8 |
| Magnesium aluminium silicate | 5 |
| Xanthan gum | 0.5 |
| Dipotassium glycyrrhizate | 0.25 |
| Zinc gluconate | 0.2 |
| Sodium methyl cocoyl taurate (30% purity) | 8 |
| Cocamidopropyl hydroxysultaine | 2 |
| Disodium EDTA | 0.1 |
| Poloxamer 124 | 0.2 |
| Propylene glycol | 2 |
| PEG-75 | 2 |
| Pentylene glycol | 3 |

-continued

| Composition | % w/w |
|---|---|
| Caprylyl glycol | 0.50 |
| BPO | 2.6 |
| Citric acid | 0.15 |
| Fragrance | 0.25 |
| PEG-40 hydrogenated castor oil | 0.25 |

Example 11

| Composition | % w/w |
|---|---|
| Purified water | QSAD 100 |
| Polyglyceryl-10 myristate | 2 |
| Hydrogenated polyisobutene | 8 |
| Magnesium aluminium silicate | 5 |
| Xanthan gum | 0.5 |
| Dipotassium glycyrrhizate | 0.25 |
| Zinc gluconate | 0.2 |
| Sodium C14-C16 olefin sulfonate | 2 |
| Disodium EDTA | 0.1 |
| Poloxamer 124 | 0.2 |
| Propylene glycol | 2 |
| PEG-75 | 2 |
| Phenoxyethanol | 0.8 |
| BPO | 2.6 |
| Citric acid | 0.15 |

Example 12

| Composition | % w/w |
|---|---|
| Purified water | QSAD 100 |
| Glycerin& caprylic/capric triglycerides & aqua & sucrose laurate | 2 |
| Hydrogenated polyisobutene | 8 |
| Magnesium aluminium silicate | 5 |
| Xanthan gum | 0.5 |
| Dipotassium glycyrrhizate | 0.25 |
| Zinc gluconate | 0.2 |
| Sodium lauryl glucose carboxylate and lauryl glucoside (35% in water) | 3 |
| Disodium EDTA | 0.1 |
| Poloxamer 124 | 0.2 |
| Propylene glycol | 2 |
| PEG-75 | 2 |
| Phenoxyethanol | 0.8 |
| BPO | 2.6 |
| Citric acid | 0.15 |

Example 13

| Composition | % w/w |
|---|---|
| Purified water | QSAD 100 |
| Glycerin& caprylic/capric triglycerides & aqua & sucrose laurate | 2 |
| Hydrogenated polyisobutene | 8 |
| Pectin | 1 |
| Magnesium aluminium silicate | 5.5 |
| Dipotassium glycyrrhizate | 0.25 |
| Zinc gluconate | 0.2 |
| Sodium C14-C16 olefin sulfonate | 2 |
| Disodium EDTA | 0.1 |
| Poloxamer 124 | 0.2 |

-continued

| Composition | % w/w |
|---|---|
| Propylene glycol | 2 |
| PEG-75 | 2 |
| Phenoxyethanol | 0.8 |
| BPO | 2.6 |
| Citric acid | 0.15 |
| Fragrance | 0.25 |
| PEG-40 hydrogenated castor oil | 0.25 |

Example 15

| Composition | % w/w |
|---|---|
| Purified water | QSAD 100 |
| Sodium dilauramidoglutamide/lysine/water | 0.10 |
| Hydrogenated polyisobutene | 8 |
| Magnesium aluminium silicate | 3 |
| Xanthan gum | 0.5 |
| Dipotassium glycyrrhizate | 0.25 |
| Zinc gluconate | 0.2 |
| Sodium C14-C16 olefin sulfonate | 2 |
| Disodium EDTA | 0.1 |
| Poloxamer 124 | 0.2 |
| Propylene glycol | 2 |
| PEG-75 | 2 |
| BPO | 2.6 |
| Citric acid | 0.05 |

Chemical stability of BPO in the composition of example 15 after storage 6 months at RT and 30° C. and 1 month at 40° C.:

| Storage conditions | Assay values per interval** | | | | |
|---|---|---|---|---|---|
| | T0 | T1M/T0 | T2M/T0 | T3M/T0 | T6M/T0 |
| RT | 100 | 97.5 | 97.6 | 98.4 | 100.0 |
| 30° C. | | | | 91.7 | 91.0 |
| 40° C. | | 94.6 | | | |

**Assay value = percentage of T0.

Data indicated that BPO is chemically stable for 6 months at RT and 30° C. and 1 month at 40° C. in the formulation as described in example 15.

Example 16

| Composition | % w/w |
|---|---|
| Purified water | QSAD 100 |
| Glycerin& caprylic/capric triglycerides & aqua & sucrose laurate | 2 |
| Hydrogenated polyisobutene | 8.0 |
| Magnesium aluminium silicate | 5 |
| Xanthan gum | 0.5 |
| Dipotassium glycyrrhizate | 0.10 |
| Zinc gluconate | 0.10 |
| Sodium C14-C16 olefin sulfonate | 2 |
| Disodium EDTA | 0.1 |
| Poloxamer 124 | 0.2 |
| Propylene glycol | 2 |
| PEG 75 | 2 |
| Phenoxyethanol | 0.8 |
| BPO | 2.6 |
| Citric acid | 0.15 |

-continued

| Composition | % w/w |
|---|---|
| Fragrance | 0.25 |
| PEG-40 hydrogenated castor oil | 0.25 |

Example 17

| Composition | % w/w |
|---|---|
| Purified water | QSAD 100 |
| Glycerin& caprylic/capric triglycerides & aqua & sucrose laurate | 2 |
| Glycerin | 4.95 |
| Mineral oil | 8 |
| Magnesium aluminium silicate | 5 |
| Xanthan gum | 0.5 |
| Dipotassium glycyrrhizate | 0.60 |
| Zinc gluconate | 0.40 |
| Sodium C14-C16 olefin sulfonate | 1 |
| Decyl glucoside (55% in water) | 3 |
| Disodium EDTA | 0.1 |
| Poloxamer 124 | 0.2 |
| Propylene glycol | 2 |
| PEG-75 | 2 |
| BPO | 2.6 |
| Citric acid | 0.15 |
| Potassium sorbate | 0.1 |
| Benzyl alcohol | 0.50 |

Example 18

A comparative marketed formulation was tested. The qualitative composition is given in the table below and contains a mixture of classical emulsifiers such as PEG-100 stearate & glyceryl stearate and a cleansing surfactant, Disodium PEG-12 Dimethicone sulfosuccinate.

| Composition | % |
|---|---|
| Purified water | N/A |
| PEG-100 stearate & Glyceryl stearate | |
| Disodium PEG-12 dimethicone sulfosuccinate | |
| BPO | |
| Oil | |
| Additifs | |

N/A—Not applicable

| Storage conditions | Assay values per interval** | | | |
|---|---|---|---|---|
| | T0 | T1M | T2M | T3M |
| RT | 100 | 101.5 | 102.8 | 103.2 |
| 40° C. | | 83.2 | 64.5 | 49.3 |

**Assay value = percentage of T0.

Contrary to the composition according to the invention, stability results show that the formulation containing BPO demonstrates acceptable chemical stability for 3 months at RT but is unstable after one month at 40° C.

It has also been noted that the formulation is not a foaming composition contrary to the composition of the current invention.

Example 19

| Composition | % w/w |
|---|---|
| Purified water | QSAD 100 |
| glycerin & caprylic/capric triglycerides & aqua & sucrose laurate | 2 |
| Hydrogenated polyisobutene | 8.0 |
| Magnesium aluminium silicate | 5 |
| Xanthan gum | 0.5 |
| Dipotassium glycyrrhizate | 0.25 |
| Zinc gluconate | 0.2 |
| Sodium C14-C16 olefin sulfate | 2 |
| Disodium EDTA | 0.1 |
| Poloxamer 124 | 0.2 |
| Propylene glycol | 2 |
| PEG-75 | 2 |
| Phenoxyethanol | 0.8 |
| BPO | 5 |
| Citric acid | 0.15 |
| Fragrance | 0.25 |
| PEG-40 hydrogenated castor oil | 0.25 |

Example 20

| Composition | % w/w |
|---|---|
| Purified water | QSAD 100 |
| Glycerin & caprylic/capric triglycerides & aqua & sucrose laurate | 2 |
| Hydrogenated polyisobutene | 8 |
| Magnesium aluminium silicate | 5 |
| Xanthan gum | 0.5 |
| Sodium lauroyl methyl isethionate (85% purity) | 2.5 |
| Disodium EDTA | 0.1 |
| Poloxamer 124 | 0.2 |
| propylene glycol | 2 |
| PEG-75 | 2 |
| Phenoxyethanol | 0.8 |
| BPO | 10 |
| Citric acid | 0.15 |

Example 21

| Composition | % w/w |
|---|---|
| Purified water | QSAD 100 |
| glycerin & caprylic/capric triglycerides & aqua & sucrose laurate | 2 |
| Hydrogenated polyisobutene | 8.0 |
| Bentonite | 4.5 |
| Xanthan gum | 0.5 |
| Dipotassium glycyrrhizate | 0.25 |
| Zinc gluconate | 0.2 |
| Sodium C14-C16 olefin sulfate | 2 |
| Disodium EDTA | 0.1 |
| Poloxamer 124 | 0.2 |
| Propylene glycol | 2 |
| PEG-75 | 2 |
| Phenoxyethanol | 0.8 |
| BPO | 2.6 |
| Citric acid | 0.15 |
| Fragrance | 0.25 |
| PEG-40 hydrogenated castor oil | 0.25 |

The invention claimed is:

1. A topical wash composition consisting of:
   (a) between 1% w/w and 5% w/w benzoyl peroxide (BPO);
   (b) between 0.5% w/w and 5% w/w expressed by weight of active material relative to the total weight of the composition of at least one anionic and/or non-ionic surfactant, selected from the group consisting of zinc coceth sulfate, sodium cocoyl isethionate, and sodium lauroyl isethionate;
   (c) between 0.1% w/w and 1% w/w zinc gluconate;
   (d) between 0.1% w/w and 1% w/w dipotassium glycyrrhizate;
   (e) at least one compound selected from vegetable oils, mineral oils, animal oils, synthetics oils, silicones, and mixtures thereof;
   (f) between 5% w/w and 90% w/w water;
   (g) between 0.1% and 5% of at least one non-ionic emulsifier selected from the family of sugar ester derivatives, polyglycerol esters, gemini surfactants, and mixtures thereof; and
   (h) one or more pharmaceutically acceptable excipients selected from the group consisting of: (i) gelling agents selected from polyacrylamides, acrylates/C10-30 alkyl crosspolymer, "electrolyte-insensitive" carbomers, polysaccharides, guar gum, cellulose derivatives, magnesium aluminum silicates, neutralized polymeric sulfonic acid polymers, and mixtures thereof; (ii) wetting agents selected from the group consisting of polyoxyethylene/polyoxypropylene copolymers, propylene glycol, dipropylene glycol, lauroglycol, propylene glycol dipelargonate, ethoxydiglycol, and mixtures thereof; (iii) antioxidants selected from the group consisting of Vitamin E and its derivatives, Vitamin C and its derivatives; butylated hydroxytoluene, sodium metabisulfite, and combinations thereof; (iv) vitamins and/or vitamin derivatives selected from vitamin E and its derivatives, vitamin C and its derivatives, vitamin PP, niacinamide, and combinations thereof; (v) soothing agents and/or anti-irritants selected from the group consisting of PPG-12/SMDI copolymer, allantoin and its derivatives, hyaluronic acid, polyquaternium-51, D-panthenol, and aloe vera; (vi) lecithins and/or phospholipids; (vii) cholesterol and/or cholesterol derivatives; (viii) preservatives selected from the group consisting of benzalkonium chloride, bronopol, chlorhexidine, chlorocresol and its derivatives, ethyl alcohol, phenoxyethanol, potassium sorbate, sodium benzoate diazolidinylurea, benzyl alcohol, and parabens; (ix) acids and/or bases; (x) chelating agents; (xi) humectants; (xii) foam boosters; (xiii) foam smoothing agents (xiv) perfume solubilizing agents; (xv) polyols; and (xvi) refatting agents,
   wherein the composition does not comprise a retinoid;
   wherein the composition does not comprise ethanol; and
   wherein at least 90% of the benzoyl peroxide present at formulation remains present in the composition after three months at room temperature.

2. The composition according to claim 1, wherein the composition is a foaming composition.

3. The composition according to claim 1, wherein the composition is in the form of an oil in water emulsion.

4. The composition according to claim 1, wherein glycerin is present at a concentration of between 0.1% and 10% by weight, relative to the total weight of the composition.

5. The composition according to claim 1, wherein the benzoyl peroxide is present at a concentration of between 2.5% and 5% by weight, relative to the total weight of the composition.

6. The composition according to claim 1, wherein the concentration of zinc gluconate, expressed by weight relative to the total weight of the composition, is between 0.15% and 0.3%.

7. The composition according to claim 1, wherein the concentration of dipotassium glycyrrhizate, expressed by weight relative to the total weight of the composition, is between 0.15% and 0.3%.

8. A method of treating acne vulgaris, the method comprising administering an effective amount of the composition according to claim 1 to an individual subject in need thereof.

9. A method of treating or improving acne in the skin of an individual subject, the method comprising administering to the individual subject an effective amount of the composition according to claim 1.

10. The composition as defined in claim 1, wherein the composition is formulated for inhibiting or treating common acne.

11. The composition according to claim 1, wherein the gelling agent is Acrylamide/Sodium Acryloyldimethyl Taurate Copolymer & Isohexadecane & Polysorbate 80 or Polyacrylamide & C13-14 Isoparaffin & Laureth-7.

12. The composition according to claim 1, wherein the gelling agent is Acrylates/C10-30 Alkyl Acrylate Crosspolymer.

13. The composition according to claim 1, wherein the gelling agent is xanthan gum or pectin.

14. The composition according to claim 1, wherein the gelling agent is hydroxypropyl methylcellulose or hydroxyethylcellulose.

15. The composition according to claim 1, wherein the gelling agent is ammonium acryloyl dimethyltaureate/carboxyethyl acrylate crosspolymer.

16. The composition according to claim 1, wherein benzoyl peroxide (BPO), zinc gluconate, and dipotassium glycyrrhizate are the sole active ingredients.

17. The composition according to claim 1, wherein at least about 90% of the benzoyl peroxide in the composition remains in the composition after storage at 40° C. for one to two months.

18. The composition of claim 1, wherein the humectants are selected from the group consisting of propylene glycol, glycerin, pentylene glycol, 1-2 hexanediol, caprylyl glycol, propane-1,3-diol, or mixtures thereof.

19. The composition of claim 1, wherein the anionic and/or non-ionic surfactant is zinc coceth sulfate.

20. The composition of claim 1, wherein the composition does not comprise any gelling agents.

21. The composition of claim 1, wherein the polyoxyethylene/polyoxypropylene copolymers are poloxamers.

* * * * *